United States Patent [19]
Lillerud et al.

[11] Patent Number: 6,114,275
[45] Date of Patent: Sep. 5, 2000

[54] CRYSTALLINE METALLOPHOSPHATES

[75] Inventors: Karl Petter Lillerud; Erling N. Halvorsen; Arne Karlsson; Duncan Akporiaye; Thomas Haug, all of Oslo, Norway

[73] Assignee: Norsk Hydro ASA, Oslo, Norway

[21] Appl. No.: 09/142,497

[22] PCT Filed: Mar. 12, 1997

[86] PCT No.: PCT/NO97/00075

§ 371 Date: Apr. 12, 1999

§ 102(e) Date: Apr. 12, 1999

[87] PCT Pub. No.: WO97/33692

PCT Pub. Date: Sep. 18, 1997

[30] Foreign Application Priority Data

Mar. 13, 1996 [NO] Norway .................................... 961034

[51] Int. Cl.$^7$ .................................................. B01J 27/182
[52] U.S. Cl. ............................................ 502/214; 423/305
[58] Field of Search .................................... 423/718, 305, 423/306; 502/214

[56] References Cited

U.S. PATENT DOCUMENTS

| | | | |
|---|---|---|---|
| 4,440,871 | 4/1984 | Lok et al. | 423/305 |
| 4,786,487 | 11/1988 | Kuehl | 423/306 |
| 5,096,684 | 3/1992 | Guth et al. | 423/306 |
| 5,370,851 | 12/1994 | Wilson | 423/305 |

FOREIGN PATENT DOCUMENTS

| | | |
|---|---|---|
| 0293939 | 7/1988 | European Pat. Off. . |
| WO 93/13013 | 8/1993 | WIPO . |

OTHER PUBLICATIONS

Chemical Abstracts 114:34650z(1991), "Fluorine–19 MAS NMR studies of crystalline microporous solids synthesized in the fluoride medium", Delmotte et al., Zeolites 1990, 10(8), 778–83.

Chemical Abstracts 121:259057f (1994), "Synthesis of new microporous AlPO$_4$ and substituted derivatives with the LTA structure", Sierea et al., Microporous Mater. 1994, 3(1–2), 29–38.

*Primary Examiner*—Tom Dunn
*Assistant Examiner*—Michael Rhee
*Attorney, Agent, or Firm*—Wenderoth, Lind & Ponack L.L.P.

[57] ABSTRACT

Microporous crystalline metallophosphate composition having an essential framework structure identified by the characteristic X-ray powder diffraction reflections given in Table I, and whose chemical composition in the calcined anhydrous form expressed in terms of mole ratios of oxides is: $(M_xAl_yP_z)O_2$ where M is silicon, $x+y+z=1$, and where x, y and z represent the mole fractions of silicon, aluminium and phosphorous present in the product, and where x may have a value from 0 to 0.5, y may have a value from 0.25 to 0.5 and z may have a value from 0.25 to 0.5. The invention also describes a method for preparing the products from a reaction mixture which includes both monovalent cations and fluoride.

11 Claims, No Drawings

CRYSTALLINE METALLOPHOSPHATES

This application is the national stage of 371 of application no. PCT/NO97/00075 filed on Mar. 12, 1997.

The present invention relates in general to a crystalline metallophosphates, and more particularly to a crystalline aluminophosphates and silicoaluminophosphates of the molecular sieve type with a novel structure, denominated UiO-6 and the method for its preparation.

Microporous crystalline aluminophosphate compositions having open framework structures formed of $AlO_2$ and $PO_2$ tetrahedral units joined by the sharing of the corner oxygen atoms and characterised by having pore openings of uniform dimensions have heretofore been disclosed in a number of publications. U.S. Pat. No. 4,310,440 describes aluminophosphates which constitute a generic class of non-zeolite molecular sieve materials being capable of undergoing complete and reversible dehydration while retaining the same essential framework topology in both the anhydrous and hydrated state.

Microporous crystalline silicoaluminophosphate compositions having open framework structures formed of $AlO_2$, $PO_2$ and $SiO_2$ tetrahedral units joined by sharing of corner oxygen atoms and characterised by having pore openings of uniform dimension is earlier disclosed for example in U.S. Pat. No. 4,440,871. These products have a chemical composition on a water-free basis as follows:

$$mR:(Si_xAl_yP_z)O_2$$

where "R" represents at least one organic template material which is present in the intracrystalline pore system; "m" is the number of moles of "R" present per mole of $(Si_xAl_yP_z)O_2$ and m has a value between 0 and 0.3, the maximum value in each case being dependent on the molecular dimensions of the template material and the available pore volume in the silico-alumino-phosphate structure in question; "x", "y" and "z" are molar fractions of silicon, aluminium and phosphorus respectively, present as tetrahedral oxides. The minimum value of "x", "y" and "z" is 0.01, and the maximum value of "x" is 0.98, of "y" 0.6 and of "z" 0.52. The minimum value of "m" in the formula above is 0.02. Also the silicoaluminophosphates constitute a generic class of non-zeolite molecular sieve materials being capable of undergoing complete and reversible dehydration while retaining the same essential framework topology in both the anhydrous and hydrated state.

By the term "essential framework topology" or "essential framework structure" as used in the aforesaid patents, and also in the present specification and claims, is meant the spatial arrangement of the primary Al—O, Si—O and P—O bond linkages.

From U.S. Pat. No. 5,370,851 there is also known silico-alumino-phosphate molecular sieves of the same composition, but with different X-ray diffraction pattern. Chlorides are used in the synthesis.

WO93/13013 describes synthesis of silico-aluminophosphates with improved stability to activation and with a controlled silicon content. Hydrochloric acid is used in the synthesis. Other microporous aluminophosphates which undergo structure rearrangements, either reversibly or irreversibly, upon partial or complete dehydration are also known, for example the minerals variscite and metavaricite and certain of the synthetic metastable aluminophosphates reported by F. D'Yvoire [Bull.Soc.Chim. France, 1762 (1961)].

Synthesis of microporous crystalline silicoaluminophosphates where the reaction mixture is modified with fluoride ions, is earlier described for example in U.S. Pat. No. 4,786,487.

The present invention is directed to a microporous crystalline metallophosphate with a novel structure, UiO-6. The calcined product has an essential framework structure identified by the characteristic X-ray powder diffraction reflections given in Table I below:

TABLE I

| 2θ | d (Å) | Relative intensity |
|---|---|---|
| 6.41–7.21 | 13.78–12.25 | VS |
| 9.23–10.03 | 9.57–8.81 | M |
| 13.25–14.05 | 6.68–6.30 | VW |
| 14.86–15.66 | 5.96–5.65 | VW |
| 14.88–15.68 | 5.95–5.65 | VW |
| 17.79–18.59 | 4.98–4.77 | VW |
| 18.96–19.76 | 4.68–4.49 | VW |
| 20.18–20.98 | 4.40–4.23 | VS |
| 21.26–22.06 | 4.18–4.03 | VW |
| 22.41–23.21 | 3.96–3.83 | VW |
| 24.41–25.21 | 3.64–3.53 | VW |
| 26.28–27.08 | 3.39–3.29 | W |
| 26.3–27.1 | 3.39–3.29 | W |
| 27.09–27.89 | 3.29–3.20 | VW |
| 28.8–29.6 | 3.10–3.02 | VW |
| 29.67–30.47 | 3.01–2.93 | VW |

More specificly the product exhibits a X-ray powder diffraction pattern in calcined form which contains at least the d-spacings in Table II below:

TABLE II

UiO-6 In the as calcined form, characteristic reflections below 30 deg. 2θ.

| 2θ | d (Å) | Relative intensity |
|---|---|---|
| 6.81 | 12.97 | 85 |
| 9.63 | 9.18 | 44 |
| 13.65 | 6.48 | 5 |
| 15.26 | 6.48 | 8 |
| 15.28 | 5.80 | 8 |
| 18.19 | 5.79 | 5 |
| 19.36 | 4.87 | 14 |
| 20.58 | 4.58 | 100 |
| 21.66 | 4.31 | 9 |
| 22.81 | 4.10 | 11 |
| 24.81 | 3.90 | 10 |
| 26.68 | 3.59 | 22 |
| 26.70 | 3.34 | 21 |
| 27.49 | 3.34 | 13 |
| 29.20 | 3.24 | 7 |
| 30.07 | 3.06 | 7 |

The microporous crystalline metallophosphate composition has a chemical composition in the calcined anhydrous form expressed in terms of mole ratios of oxides:

$$(M_xAl_yP_z)O_2$$

where M is silicon, x+y+z=1, and where x, y, and z represent the mole fractions of silicon, aluminium and phosphorous present in the product, and where x may have a value from 0 to 0.5, y may have a value from 0.25 to 0.5 and z may have a value from 0.25 to 0.5.

In its as synthesised form the product exhibits a X-ray powder diffraction pattern, which contains at least the d-spacings set forth in Table III set forth below:

TABLE III

| 2θ | d (Å) | Relative intensity |
|---|---|---|
| 6.41–7.21 | 13.78–12.25 | W |
| 9.24–10.04 | 9.56–8.80 | VW |
| 14.88–15.68 | 5.95–5.65 | VW |
| 17.1–17.9 | 5.18–4.95 | VW |
| 17.78–18.58 | 4.98–4.77 | VW |
| 18.9–19.7 | 4.69–4.50 | VW |
| 19.61–20.41 | 4.52–4.35 | VW |
| 20.1–20.9 | 4.41–4.25 | VS |
| 21.2–22 | 4.19–4.04 | VW |
| 22.39–23.19 | 3.97–3.83 | VW |
| 24.2–25 | 3.67–3.56 | VW |
| 25.93–26.73 | 3.43–3.33 | VW |
| 27–27.8 | 3.30–3.21 | VW |
| 27.76–28.56 | 3.21–3.12 | VW |
| 28.73–29.53 | 3.10–3.02 | VW |
| 28.81–29.61 | 3.10–3.01 | VW |

More specificly the product exhibits a X-ray powder diffraction pattern in as synthesised form which contains at least the d-spacings in Table IV below:

TABLE IV

UiO-6 In the as synthesised form, characteristic reflections below 30 deg. 2θ.

| 2θ | d (Å) | Relative intensity |
|---|---|---|
| 6.81 | 12.96 | 38 |
| 9.64 | 9.17 | 21 |
| 15.28 | 5.80 | 5 |
| 17.50 | 5.06 | 5 |
| 18.18 | 4.88 | 5 |
| 19.30 | 4.60 | 14 |
| 20.01 | 4.43 | 8 |
| 20.50 | 4.33 | 100 |
| 21.60 | 4.11 | 6 |
| 22.79 | 3.90 | 12 |
| 24.60 | 3.62 | 8 |
| 26.33 | 3.38 | 14 |
| 27.40 | 3.25 | 16 |
| 28.16 | 3.17 | 5 |
| 29.13 | 3.06 | 9 |
| 29.21 | 3.05 | 9 |

In the as synthesised form the composition expressed in terms of mole ratios of oxides is:

$$mR(M_xAl_yP_z)O_2$$

where M is silicon, R is at least one organic template, m may have a value from 0.02 to 0.3, x+y+z=1 where x, y and z represent the mole fractions of silicon, aluminium and phosphorous present in the product, and where x may have a value from 0 to 0.5, y may have a value from 0.25 to 0.5 and z may have a value from 0.25 to 0.5 and where a monovalent cation and one reactive form of fluoride is present in an effective amount to form the product.

The invention also concerns a method for preparing a microporous crystalline metallophosphate composition. UIO-6 can be prepared by hydrothermal crystallisation from a reaction mixture prepared by combining reactive sources of phosphorus and aluminium with water and hydrofluoric acid and at least one structure directing agent ("templating agent" or "template") which can include organic amines and quartenary ammonium compounds, and most preferably tetraethylammonium hydroxide. The synthesis of the products is unusual in that the aluminophosphategel containing the organic amine has to be modified with both fluoride and an inorganic (or NH4+) cation.

In the as-synthesised form wherein the product prepared by hydrothermal crystallisation has not been subjected to a post-synthesis treatment effective in removing any non-framework constituents, both the organic (template) structure directing agent, inorganic ions (if present in the synthesis gel) and fluorine is contained within the framework structure of the aluminophosphate. The non framework constituents is readily removed by calcination and washing and does not appear to be an essential constitute of the final product.

The preparative process typically comprises forming a reaction mixture which in terms of molar ratios of oxides is $1.0Al_2O_3:0.5-1.3$ $P_2O_5:0—0-1.2$
$SiO_2:0.5-3R:0-1.0HF:0-0.5M:7-200 H_2O$ and contains at least one organic templating agent (R), a monovalent cation (M) and one reactive form of fluoride in an effective amount which forms UIO-6 product. Representative of the amount of organic template employed herein is an amount between 0.5 and about 3 moles of organic templating agent and 0.05 to 1 moles of F– per mole of $Al_2O_3$. The reaction mixture is placed in a reaction vessel inert toward the reaction mixture and heated at a temperature of at least about 70° C., preferably between 75° C. and 200° C. under autogenous pressure, until crystallised, usually a period from 2 hours to 3 weeks or more. The solid crystalline reaction product is then recovered by any convenient method, such as filtration or centrifugation, washed with water and dried in air at a temperature between ambient and about 110° C.

In a preferred crystallisation method, a solution is prepared from aqueous solution of phosphoric acid, hydrofluoric acid, and an organic templating agent and is then heated to about 120° C. from 1 to 4 days. The preferred ratio of inorganic oxides in the initial solution is:

$Al_2O_3:0.6-1$ $P_2O_5:0-0.4$ $SiO_2:40-60 H_2O$

The preferred initial solution contains between 0.5 and 1 moles of organic templating agent, 0.2 to 0.7 moles of F– and 0 to 0.5 moles of cations per mole of $Al_2O_3$.

Not all templating agents suitably employed in preparation of all aluminophosphates are believed to be generally suitable for the preparation of UIO-6. The use of tetraethylammoium hydroxide has been found to act as an acceptable templating agent for use in the preparation of the products.

The as-synthesized compositions are isolated after synthesis and advantageously washed with water. The as-synthesized compositions may contain the organic templating agent within the intracrystalline pore system. The form of the organic templating agent may be an occluded molecular species (or may be present as a charge balancing cation). In general, it is desirable to remove the organic templating agent by calcination at a temperature sufficient to remove substantially all of the organic templating agent. The calcination temperature is generally between 300° C. and about 700° C., i.e., whereby the organic templating agent is removed by thermal degradation.

All X-ray patterns appearing herein were obtained by use of a standard X-ray powder diffraction technique using a Siemens D500 powder diffractometer equipped with a Cu, X-ray tube and a Ge-monochromator ensuring strictly monochromatic Cu-α1 radiation.

Intensities were determined from the heights of diffraction peaks after subtracting background, the intensity of each of the other peaks are in % of the intensity of the strongest line or peak.

As will be understood by those skilled in the art the parameters 2 theta and Intensity, irrespective of the technique employed, is subjected to both human and mechanical error, which in combination, can impose an uncertainty of about 0.4° on each reported value of 2 theta. This uncertainty is of course, also manifested in the reported value of the d-spacings, which are calculated from the 2 theta values. The observed relative intensities are in addition to experimental uncertainty sensitive to the water filling in the microporous volume in these materials and might therefore show large deviations caused by the degree of drying of the material and relative humidity in the laboratory air at the time the data are recorded. This impression is general throughout the art and is not sufficient to preclude the differentiation of the present crystalline materials from the compositions of the prior art.

When the as-synthesized compositions are calcined, i.e., heated at a temperature sufficiently high (typically about 300° C. and 700° C.) or otherwise treated, such as by chemical oxidation, to remove essentially all of the organic templating agent present in the intracrystalline pore system and are allowed to rehydrate in ambient air, the composition has an x-ray powder diffraction pattern which contains at least the d-spacings set forth in Table I and Table II.

UIO-6 exhibits surface characteristics which make it useful as a catalyst or catalyst support in various hydrocarbon conversion and oxidative combustion processes. The products can be associated with catalytically active metals, e.g., by framework substitution, by impregnation, doping and the like, by methods traditionally used in the art for fabrication of catalyst compositions.

Among the hydrocarbon conversion reaction reactions that can be catalysed by the new compositions are cracking, hydrocracking, alkylation for both the aromatic and isoparaffin types, isomerization including xylene isomerizatio , polymerisation, reforming, hydrogenation, dehydrogenation, transalkylation, dealkylation, hydrodecyclization and dehydrocyclization.

The results further shows that UIO-6 have a pore size of at approximately 6.2 Ångstrøm which make them suitable for use as a molecular sieve for the separation of molecular species, and carrying out shape-selective catalysis.

The following examples are provided to illustrate the invention and are not to be construed as limiting thereof:

ABBREVIATIONS USED

In the following examples the UIO-6 compositions were prepared using numerous reagents. The reagents employed and their abbreviations, if any, along with other abbreviations used are as follows:

a) LOI: Loss On Ignition;
b) $H_3PO_4$: 85 weight percent aqueous phosphoric acid;
c) TEAOH: Aqueous solution of tetraethylammoium hydroxide;
d) Ludox: Colloidal silica
e) TEFLON (polytetrafluoroethylene): is a trademark of E.I. du Pont de Nemours & Co, Wilmington, Del., U.S.A; and
f) HF: 48 weight percent aqueous solution of hydrofluoric acid.

Impurity Phases

As will be understood by those skilled in the art, other phases than UiO-6 might appear in the product. From these impurity phases only some and the strongest lines, will be visible in the diffraction pattern. This will be dependent on the amount of impurity phases in the product. The impurities found are $AlPO_4$-5 (U.S. Pat. No. 4,310,440), SAPO-5 and SAPO 20 (both U.S. Pat. No. 4,440,871) and UiO-4 (to be published).

TABLE V

Characteristic reflections below 30 deg 2θ. in the $AlPO_4$-5/SAPO-5 phase in the as -synthesised form.

| 2θ | d (Å) | Relative Intensity |
| --- | --- | --- |
| 7.40 | 11.94 | 83 |
| 12.86 | 6.88 | 14 |
| 14.86 | 5.96 | 24 |
| 19.72 | 4.50 | 63 |
| 20.98 | 4.23 | 67 |
| 22.38 | 3.97 | 100 |
| 24.70 | 3.60 | 7 |
| 25.94 | 3.43 | 40 |
| 29.00 | 3.08 | 18 |
| 30.06 | 2.97 | 23 |

TABLE VI

Characteristic reflections below 30 deg. 2θ in the UiO-4 phase in the as synthesised form.

| 2θ | d (Å) | Relative Intensity |
| --- | --- | --- |
| 4.87 | 18.13 | 15 |
| 7.21 | 12.26 | 2 |
| 9.62 | 9.18 | 100 |
| 9.73 | 9.08 | 100 |
| 11.51 | 7.68 | 6 |
| 12.50 | 7.08 | 8 |
| 13.01 | 6.80 | 5 |
| 13.33 | 6.64 | 11 |
| 14.09 | 6.28 | 16 |
| 14.25 | 6.21 | 22 |
| 14.81 | 5.98 | 10 |
| 15.65 | 5.66 | 35 |
| 16.14 | 5.49 | 30 |
| 16.89 | 5.24 | 27 |
| 17.71 | 5.00 | 4 |
| 18.44 | 4.81 | 50 |
| 20.33 | 4.37 | 16 |
| 20.44 | 4.34 | 29 |
| 20.83 | 4.26 | 22 |
| 20.89 | 4.25 | 32 |
| 21.16 | 4.20 | 37 |
| 21.39 | 4.15 | 13 |
| 21.72 | 4.09 | 4 |
| 22.10 | 4.02 | 6 |
| 22.51 | 3.95 | 9 |
| 23.25 | 3.82 | 12 |
| 23.65 | 3.76 | 7 |
| 24.06 | 3.70 | 6 |
| 24.44 | 3.64 | 6 |
| 25.37 | 3.51 | 13 |
| 25.54 | 3.49 | 13 |
| 25.98 | 3.43 | 21 |
| 26.19 | 3.40 | 8 |
| 26.89 | 3.31 | 9 |
| 27.19 | 3.28 | 9 |

TABLE VII

Characteristic reflections below 30 deg 2θ in the SAPO-20 phase in the as synthesised form.

| 2θ | d (Å) | Relative Intensity |
| --- | --- | --- |
| 14.09 | 6.28 | 40 |
| 19.89 | 4.46 | 41 |
| 22.21 | 4.00 | 5 |
| 24.37 | 3.65 | 100 |
| 28.18 | 3.16 | 13 |

EXAMPLE 1
Preparation of AlPO$_4$ UIO-6

A reaction mixture was prepared by combining 3.71 g of a pseudo-boehmite phase (73.2wt. % Al$_2$O$_3$) and 8.50 g H$_2$O to which was added 6.20 g of 85 wt. % orthophosphoric acid (H$_3$PO$_4$), and stirred until homogeneous. Into this mixture was blended 0.27 g of 48 wt. % hydrofluoric acid (HF). Then it was added 11.32 g of 35 wt. % aqueous tetraethylammonium hydroxide (TEAOH) and stirred until homogeneous. The composition of the final mixture, in terms of molar oxide ratios was:

1.0 Al$_2$O$_3$:1.0 P$_2$O$_5$:1.0 TEAOH:0.2 HF:40 H$_2$O

The reaction mixture (30 g) was sealed in a Teflon jar and heated in a oven at 120° C. for 24 hours. The solids were recovered by centrifugation, washed with H$_2$O, and dried in air at ambient temperature.

The 3.2 g of dried product had an x-ray powder diffraction pattern which indicated UIO-6 with a small amount of AlPO$_4$-5 and UiO-4 impurity phases. The characteristic reflections to these impurity phases are given in Table V and Table VI, respectively.

EXAMPLE 2
Preparation of AlPO$_4$ UiO-6

A reaction mixture was prepared by combining 3.67 g of a pseudo-boehmite phase (73.2 wt % Al$_2$O$_3$) and 8.32 g H$_2$O to which was added 6.13 g of 85 wt. % orthophosphoric acid (H$_3$PO$_4$), and stirred until homogenous. To this mixture was added a mixture containing 0.31 g of KF, 0.40 g of 35 wt. % hydrofluoric acid (HF) and 11.18 g of 35 wt % aqueous tetraethylammonium hydroxide (TEAOH), and the whole reaction mixture was stirred until homogeneous. The composition of the final mixture, in terms of molar oxide ratios was:

1.0 Al$_2$O$_3$:1.0 P$_2$O$_5$:1.0 TEAOH:0.5 HF:0.2 KF:40 H$_2$O

The reaction mixture (approx. 30 g) was sealed in a Teflon jar and heated in an oven at 150° C. for 24 hours. The solids were recovered by centrifugation, washed with H$_2$O and dried in air at ambient temperature.

Both fluoride and cations were incorporated in the as-synthesised material, having the following composition: $\{(C_2H_5)_4N^+K_{1.5}{}^+F^-_3\}$ [Al$_{16}$P$_{16}$O$_{32}$]6H$_2$O The 3 g of dried product had an x-ray powder diffraction pattern which indicated UIO-6 with a small amount of AlPO$_4$-5 phase. The characteristic reflections to this impurity phase are given in Table V.

EXAMPLE 3
Preparation of AlPO$_4$ UiO-6

A reaction mixture was prepared by combining 3.22 g of a pseudo-boehmite phase (73.2 wt % Al$_2$O$_3$) and 12.13 g H$_2$O to which was added 5.37 g of 85 wt. % orthophosphoric acid (H$_3$PO$_4$), and stirred until homogenous. To this mixture was added a mixture containing 0.10 g of NaF, 0.35 g of 35 wt. % hydrofluoric acid (HF) and 8.83 g of 35 wt % aqueous tetraethylammonium hydroxide (TEAOH), and the whole reaction mixture was stirred until homogeneous. The composition of the final mixture, in terms of molar oxide ratios was:

1.0 Al$_2$O$_3$:1.0 P$_2$O$_5$:0.9 TEAOH:0.4 HF:0.1 NaF:50 H$_2$O

The reaction mixture (approx. 30 g) was sealed in a Teflon jar and heated in an oven at 150 ° C. for 48 hours. The solids were recovered by centrifugation, washed with H$_2$O and dried in air at ambient temperature. The 3 g of dried product had an x-ray powder diffraction pattern which indicated UIO-6.

Both fluoride and cations were incorporated in the as-synthesised material, having the following composition: $\{(C_2H_5)_4 N^+Na_{0.5}{}^+F_{1.5}\}$ [Al$_{16}$P$_{16}$O$_{32}$]3 H$_2$O A portion of the calcined UIO-6 was placed in a standard Stanton Redcroft thermo-gravimetric apparatus and activated at 450° C. in dry nitrogen overnight. Subsequent adsorption data were measured as listed in Table VIII below. Activation at 400° C. in dry nitrogen was performed between all adsorbate changes.

TABLE VIII

| | Adsorption in UiO-6. | | |
|---|---|---|---|
| Adsorbate molecule | Kinetic diameter (Å) | Temperature (° C.) | Weight % Adsorbed |
| 1,3,5 trimethyl-benzene | 6.0 | 27 | 4 |
| isobutane | 5.0 | 25 | 5 |
| n-hexane | 4.3 | 25 | 6.2 |
| H$_2$O | 2.6 | 25 | 30.5 |

These adsorption data indicate that the UIO-6 product is a molecular sieve with a pore size of at least 6.0 Ångstrøm.

The structure of UIO-6 has been solved and it has been found that it has a unidimensional 12-ring structure with channels with 6.2 Ångstrøm free aperture.

EXAMPLE 4
Preparation of SAPO$_4$ UiO-6

A reaction mixture was prepared by combining 3.17 g of a pseudo-boehmite phase (73.2 wt % Al$_2$O$_3$) and 10.85 g H$_2$O to which was added 5.29 g of 85 wt. % orthophosphoric acid (H$_3$PO$_4$), and stirred until homogenous and 0.57 g of 40 wt. % HF was blended into this mixture then 0.46 g of Ludox LS (30% SiO$_2$) was added to the gel. To this mixture was added 9.66 g of 35 wt % aqueous tetraethylammonium hydroxide (TEAOH), and the whole reaction mixture was stirred until homogeneous. The composition of the final mixture, in terms of molar oxide ratios was:

1.0 Al$_2$O$_3$:1.0 P$_2$O$_5$:0.1 SiO$_2$:1.0 TEAOH:0.5 HF:50 H$_2$O

The reaction mixture (approx. 30 g) was sealed in a Teflon jar and heated in an oven at 150° C. for 21 hours. The solids were recovered by centrifugation, washed with H$_2$O and dried in air at ambient temperature.

The 1.6 g of dried product had an x-ray powder diffraction pattern which indicated UIO-6 with a small amount of SAPO$_4$-5, UiO-4 and SAPO-20 impurity phases. The characteristic reflections to these impurity phases are given in Table V, Table VI and Table VII, respectively.

EXAMPLE 5
Preparation of SAP$_4$ UiO-6

A reaction mixture was prepared by combining 3.12 g of a pseudo-boehmite phase (73.2 wt % Al$_2$O$_3$) and 11.24 g H$_2$O to which was added 5.27 g of 85 wt. % orthophosphoric acid (H$_3$PO$_4$), and -stirred until homogenous and 0.24 g of 40 wt. % HF was blended into this mixture then 1.36 g of Ludox LS (30% SiO$_2$) was added to the gel. To this mixture was added 8.60 g of 35 wt % aqueous tetraethylammonium hydroxide (TEAOH), and the whole reaction mixture was stirred until homogeneous. The composition of the final mixture, in terms of molar oxide ratios was:

1.0 Al$_2$O$_3$:0.7 P$_2$O$_5$:0.3 SiO$_2$:0.9 TEAOH:0.2 HF:0.3 NaF:50 H$_2$O

The reaction mixture (approx. 30 g) was sealed in a Teflon jar and heated in an oven at 150 ° C. for 48 hours. The solids were recovered by centrifugation, washed with H$_2$O and dried in air at ambient temperature.

The 2.6 g of dried product had an x-ray powder diffraction pattern which indicated UIO-6 with a small amount of UiO-4 impurity phase. The characteristic reflections to these impurity phase are given in Table VI.

EXAMPLE 6

Preparation of SAPO$_4$ UiO-6

A reaction mixture was prepared by combining 3.72 g of a pseudo-boehmite phase (73.2 wt % Al$_2$O$_3$) and 9.5 g H$_2$O to which was added 6.31 g of 85 wt. % orthophosphoric acid (H$_3$PO$_4$), and stirred until homogenous and 0.24 g of 40 wt. %. HF was blended into this mixture then 0.52 g of Ludox LS (30% SiO$_2$) was added to the gel. To this mixture was added 10.2 g of 35 wt % aqueous tetraethylammonium hydroxide (TEAOH), and the whole reaction mixture was stirred until homogeneous. The composition of the final mixture, in terms of molar oxide ratios was:

1.0 Al$_2$O$_3$:0.7 P$_2$O$_5$:0.1 SiO$_2$:0.9 TEAOH:0.2 HF:0.3 NaF:40 H$_2$O

The reaction mixture (approx. 30 g) was sealed in a Teflon jar and heated in an oven at 150° C. for 68 hours. The solids were recovered by centrifugation, washed with H$_2$O and dried in air at ambient temperature.

The 4.7 g of dried product had an X-ray powder diffraction pattern which indicated a nearly pure UiO-S6 with a minor amount of an SAPO-5 impurity phase. The characteristic reflections to these impurity phase are given in Table V.

The chemical composition of UiO-6 made from example 6 is:

| Element | Element % | Atom % |
|---------|-----------|--------|
| O | 48.77 | 62.60 |
| F | 1.76 | 1.90 |
| Na | 1.73 | 1.54 |
| Al | 23.16 | 17.63 |
| Si | 0.38 | 0.28 |
| P | 24.41 | 16.05 |

What is claimed is:

1. A microporous crystalline metallophosphate composition, having an essential framework structure in calcined form identified by the characteristic X-ray powder diffraction reflections given in Table I:

| 2θ | d (Å) | Relative intensity |
|-----|-------|--------------------|
| 6.41–7.21 | 13.78–12.25 | VS |
| 9.23–10.03 | 9.57–8.81 | M |
| 13.25–14.05 | 6.68–6.30 | VW |
| 14.86–15.66 | 5.96–5.65 | VW |
| 14.88–15.68 | 5.95–5.65 | VW |
| 17.79–18.59 | 4.98–4.77 | VW |
| 18.96–19.76 | 4.68–4.49 | VW |
| 20.18–20.98 | 4.40–4.23 | VS |
| 21.26–22.06 | 4.18–4.03 | VW |
| 22.41–23.21 | 3.96–3.83 | VW |
| 24.41–25.21 | 3.64–3.53 | VW |
| 26.28–27.08 | 3.39–3.29 | W |
| 26.3–27.1 | 3.39–3.29 | W |
| 27.09–27.89 | 3.29–3.20 | VW |
| 28.8–29.6 | 3.10–3.02 | VW |
| 29.67–30.47 | 3.01–2.93 | VW |

2. The microporous crystalline metallophosphate composition according to claim 1, having an essential framework structure identified by the characteristic X-ray powder diffraction reflections given in Table II:

| 2θ | d (Å) | Relative intensity |
|-----|-------|--------------------|
| 6.81 | 12.97 | 85 |
| 9.63 | 9.18 | 44 |
| 13.65 | 6.48 | 5 |
| 15.26 | 6.48 | 8 |
| 15.28 | 5.80 | 8 |
| 18.19 | 5.79 | 5 |
| 19.36 | 4.87 | 14 |
| 20.58 | 4.58 | 100 |
| 21.66 | 4.31 | 9 |
| 22.81 | 4.10 | 11 |
| 24.81 | 3.90 | 10 |
| 26.68 | 3.59 | 22 |
| 26.70 | 3.34 | 21 |
| 27.49 | 3.34 | 13 |
| 29.20 | 3.24 | 7 |
| 30.07 | 3.06 | 7 |

3. The microporous crystalline metallophosphate composition according to claim 1, wherein that its chemical composition in the calcined anhydrous form expressed in terms of mole ratios of oxides is:

$$(M_xAl_yP_z)O_2$$

where M is silicon, x+y+z=1, and where x, y, and z represent the mole fractions of silicon, aluminium and phosphorous present in the product, and where x may have a value from 0 to 0.5, y may have a value from 0.25 to 0.5 and z may have a value from 0.25 to 0.5.

4. A microporous crystalline metallophosphate composition wherein its chemical composition in as synthesised form expressed in terms of mole ratios of oxides is:

$$mR(M_xAl_yP_z)O_2$$

where M is silicon, R is at least one organic template, m may have a value from 0.02 to 0.3, x+y+z=1 where x, y and z represent the mole fractions of silicon, aluminium and phosphorous present in the product, and where x may have a value from 0 to 0.5, y may have a value from 0.25 to 0.5 and z may have a value from 0.25 to 0.5 and where a monovalent cation and one reactive form of fluoride is present in an effective amount to form the product, and where the product has an essential framework structure identified by the characteristic X-ray powder diffraction reflections given in Table III:

| 2θ | d (Å) | Relative intensity |
|-----|-------|--------------------|
| 6.41–7.21 | 13.78–12.25 | W |
| 9.24–10.04 | 9.56–8.80 | VW |
| 14.88–15.68 | 5.95–5.65 | VW |
| 17.1–17.9 | 5.18–4.95 | VW |
| 17.78–18.58 | 4.98–4.77 | VW |
| 18.9–19.7 | 4.69–4.50 | VW |
| 19.61–20.41 | 4.52–4.35 | VW |
| 20.1–20.9 | 4.41 A.25 | VS |
| 21.2–22 | 4.19–4.04 | VW |
| 22.39–23.19 | 3.97–3.83 | VW |
| 24.2–25 | 3.67–3.56 | VW |
| 25.93–26.73 | 3.43–3.33 | VW |
| 27–27.8 | 3.30–3.21 | VW |
| 27.76–28.56 | 3.21–3.12 | VW |
| 28.73–29.53 | 3.10–3.02 | VW |
| 28.81–29.61 | 3.10–3.01 | VW |

5. The microporous crystalline metallophosphate composition in as synthesised form according to claim 4, having an essential framework structure identified by the characteristic X-ray powder diffraction reflections given in Table IV:

| 2θ | d (Å) | Relative intensity |
|---|---|---|
| 6.81 | 12.96 | 38 |
| 9.64 | 9.17 | 21 |
| 15.28 | 5.80 | 5 |
| 17.50 | 5.06 | 5 |
| 18.18 | 4.88 | 5 |
| 19.30 | 4.60 | 14 |
| 20.01 | 4.43 | 8 |
| 20.50 | 4.33 | 100 |
| 21.60 | 4.11 | 6 |
| 22.79 | 3.90 | 12 |
| 24.60 | 3.62 | 8 |
| 26.33 | 3.38 | 14 |
| 27.40 | 3.25 | 16 |
| 28.16 | 3.17 | 5 |
| 29.13 | 3.06 | 9 |
| 29.21 | 3.05 | 9 |

6. A method for preparing a microporous crystalline metallophosphate composition according to any one of claims 1–5 wherein a reaction mixture is formed having a composition in terms of mole ratios of 1.0 $Al_2O_3$:0.5–1.3 $P_2O_5$:0–1.2 $SiO_2$:0.5–3 R:0.05–1.0 HF:0–0.5 M:7–200 $H_2O$, where R is at least one organic templating agent, and M is a monovalent cation and heating the reaction mixture thus formed at a temperature of at least 70° C. to about 200° C. under autogenous pressure until crystals of said metallophosphate are formed.

7. A method according to claim 6, wherein the reaction mixture used comprises the following composition of inorganic oxides: $Al_2O_3$:0.6–1 $P_2O_5$:0–0.4 $SiO_2$:40–60 $H_2O$ and further contains between 0.5 and 1 moles of an organic templating agent, 0.2 to 0.7 moles of F– and 0 to 0.5 moles of cations per mole of $Al_2O_3$.

8. The method according to claim 6, wherein the organic templating agent used is an organic amine or a quaternary ammonium compound.

9. The method according to claim 6, wherein the monovalent cation is selected from the group consisting of sodium, potassium and ammonium.

10. The method according to claim 8, wherein the organic templating agent is tetraethylammonium hydroxide.

11. The microporous crystalline metallophosphate composition according to claim 2, wherein its chemical composition in the calcined anhydrous form expressed in terms of mole ratios of oxides is:

$$(M_xAl_yP_z)O_2$$

where M is silicon, x+y+z=1, and where x, y, and z represent the mole fractions of silicon, aluminium and phosphorous present in the product, and where x may have a value from 0 to 0.5, y may have a value from 0.25 to 0.5 and z may have a value from 0.25 to 0.5.

* * * * *